(12) United States Patent
Rotroff et al.

(10) Patent No.: US 12,205,686 B2
(45) Date of Patent: Jan. 21, 2025

(54) IDENTIFYING PATIENTS FOR INTENSIVE HYPERGLYCEMIA MANAGEMENT

(71) Applicant: THE CLEVELAND CLINIC FOUNDATION, Cleveland, OH (US)

(72) Inventors: Daniel M. Rotroff, Pepper Pike, OH (US); Kevin M. Pantalone, Stow, OH (US); Galen Miller-Atkins, Cleveland, OH (US); Arshiya Mariam, Grafton, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 1001 days.

(21) Appl. No.: 17/187,782

(22) Filed: Feb. 27, 2021

(65) Prior Publication Data

US 2021/0272661 A1    Sep. 2, 2021

Related U.S. Application Data

(60) Provisional application No. 62/982,195, filed on Feb. 27, 2020.

(51) Int. Cl.
*G16H 10/40* (2018.01)
*G16B 40/00* (2019.01)
(Continued)

(52) U.S. Cl.
CPC ............ *G16H 10/40* (2018.01); *G16B 40/00* (2019.02); *G16H 10/60* (2018.01); *G16H 15/00* (2018.01); *G16H 50/30* (2018.01)

(58) Field of Classification Search
CPC ........ G16H 10/40; G16H 10/60; G16H 15/00; G16H 50/30; G16H 20/00; G16B 40/00
See application file for complete search history.

(56) References Cited

U.S. PATENT DOCUMENTS 7,824,333 B2 * 11/2010 Otto ................. G16H 10/40
                                                    600/365
10,332,615 B2 * 6/2019 Kovatchev ........... A61B 5/7267
(Continued)

FOREIGN PATENT DOCUMENTS

EP    2535831 A1 * 12/2012    ......... G06F 19/3456
EP    3544017 A1 *  9/2019    ......... G06F 19/3456
(Continued)

OTHER PUBLICATIONS

Jiang et al., "Obesity, clinical, and genetic predictors for glycemic progression in Chinese patients with type 2 diabetes: A cohort study using the Hong Kong Diabetes Register and Hong Kong Diabetes Biobank" (English), Jul. 2020, PLoS Medicine, 17(7), e1003209. (Year: 2020).*

(Continued)

*Primary Examiner* — Mohammad Ali
*Assistant Examiner* — Kelvin Booker
(74) *Attorney, Agent, or Firm* — Tarolli, Sundheim, Covell & Tummino LLP

(57) ABSTRACT

Systems and methods are provided for assigning a treatment to a patient is provided. A set of genetic data representing a patient. A polygenic score representing the likelihood that a patient will benefit from intensive glycemia treatment is generated from the set of genetic data. A parameter representing a response of the patient to intensive glycemia treatment is assigned according to the polygenic score.

19 Claims, 7 Drawing Sheets

(51) Int. Cl.
    *G16H 10/60*     (2018.01)
    *G16H 15/00*     (2018.01)
    *G16H 50/30*     (2018.01)

(56) References Cited

U.S. PATENT DOCUMENTS

| | | | | |
|---|---|---|---|---|
| 2005/0209148 | A1* | 9/2005 | Rosenthal | A61P 3/00 514/6.9 |
| 2006/0062859 | A1* | 3/2006 | Blum | A61K 45/06 424/769 |
| 2007/0232876 | A1* | 10/2007 | Otto | G16H 20/17 600/365 |
| 2009/0299645 | A1* | 12/2009 | Colby | G16B 20/10 506/7 |
| 2010/0324401 | A1* | 12/2010 | Otto | G16H 20/00 600/365 |
| 2014/0187519 | A1* | 7/2014 | Cooke | G01N 33/6893 514/263.36 |
| 2015/0310178 | A1* | 10/2015 | Minor | G16Z 99/00 702/19 |
| 2018/0186797 | A1* | 7/2018 | Ren | C07D 487/06 |
| 2018/0366223 | A1* | 12/2018 | Breton | G16H 50/20 |
| 2019/0017119 | A1* | 1/2019 | Khera | C12Q 1/6886 |
| 2019/0156919 | A1* | 5/2019 | Magis | G16B 50/00 |
| 2019/0214147 | A1* | 7/2019 | Ariely | G16H 10/40 |
| 2019/0330698 | A1* | 10/2019 | Khera | A61K 38/28 |

FOREIGN PATENT DOCUMENTS

| | | | | |
|---|---|---|---|---|
| WO | WO-2006072654 | A1 * | 7/2006 | A61P 3/08 |
| WO | WO-2015079079 | A1 * | 6/2015 | G16H 50/20 |
| WO | WO-2015148387 | A2 * | 10/2015 | G06F 19/00 |

OTHER PUBLICATIONS

He et al., "Intensive Glucose Control Reduces the Risk Effect of TRIB3, SMARCD3, and ATF6 Genetic Variation on Diabetic Vascular Complications" (English), Dec. 2018, Frontiers in Pharmacology, 9, 1422. (Year: 2018).*
Gibson, G., "On the utilization of polygenic risk scores for therapeutic targeting", Apr. 2019, https://doi.org/10.1371/journal.pgen.1008060. (Year: 2019).*
Padilla-Martinez et al., "Systematic Review of Polygenic Risk Scores for Type 1 and Type 2 Diabetes", Feb. 2020, Int. J. Mol. Sci. 2020, 21, 1703; doi: 10.3390/ijms21051703. (Year: 2020).*
Tremblay et al., "Polygenic risk scores predict diabetic complications and their response to therapy", Nov. 2019, CC-BY-NC-ND 4.0 International license. (Year: 2019).*
Khera et al., "Genome-wide polygenic scores for common diseases identify individuals with risk equivalent to monogenic mutations", Sep. 2018, Nature Genetics, vol. 50, 1219-1224. (Year: 2018).*
Udler et al., "Genetic Risk Scores for Diabetes Diagnosis and Precision Medicine", Jul. 2019. (Year: 2019).*
Hodgson et al., "Integrating polygenic risk scores in the prediction of type 2diabetes risk and subtypes in British Pakistanis and Bangladeshis: A population-based cohort study", Aug. 2021, https://doi.org/10.1371/journal.pmed.1003981. (Year: 2021).*
Hornbak et al., "A Combined Analysis of 48 Type 2 Diabetes Genetic Risk Variant Shows No. Discriminative Value to Predict Time to Firs Prescription of a Glucose Lowering Drug in Danish Patients with Screen Detected Type 2 Diabetes", Apr. 2014, https://doi.org/10.1371/journal.pone.0104837. (Year: 2014).*
Karthikeyan et al., "Rule Based System for Better Prediction of Diabetes", 2019, 3rd International Conference on Computing and Communication Technologies ICCCT 2019. (Year: 2019).*
Pantalone et al., "The Probability of A1C Goal Attainment in Patients With Uncontrolled Type 2 Diabetes in a Large Integrated Delivery System", May 2019, Diabetes Care 2020;43:1910-1919 | https://doi.org/10.2337/dc19-0968. (Year: 2019).*
Advance Collaborative Group, Patel A, MacMahon S, Chalmers J, Neal B, Billot L, Woodward M, Marre M, Cooper M, Glasziou P, Grobbee D, Hamet P, Harrap S, Heller S, Liu L, Mancia G, Mogensen CE, Pan C, Poulter N, Rodgers A, Williams B, Bompoint S, de Galan BE, Joshi R, Travert F. Intensive blood glucose control and vascular outcomes in patients with type 2 diabetes. N Engl J Med. Jun. 12, 2008;358(24):2560-72. doi: 10.1056/NEJMoa0802987. Epub Jun. 6, 2008. PMID: 18539916.
Petitjean, François, Alain Ketterlin, and Pierre Gancarski. "A global averaging method for dynamic time warping, with applications to clustering." Pattern recognition 44.3 (2011): 678-693.
Keogh, Eamonn J., and Michael J. Pazzani. "Scaling up dynamic time warping for datamining applications." Proceedings of the sixth ACM SIGKDD international conference on Knowledge discovery and data mining. 2000.
Petitjean, François, et al. "Faster and more accurate classification of time series by exploiting a novel dynamic time warping averaging algorithm." Knowledge and Information Systems 47.1 (2016): 1-26.
Rani, Sangeeta, and Geeta Sikka. "Recent techniques of clustering of time series data: a survey." International Journal of Computer Applications 52.15 (2012).
Benjamini, Yoav, and Yosef Hochberg. "Controlling the false discovery rate: a practical and powerful approach to multiple testing." Journal of the Royal statistical society: series B (Methodological) 57.1 (1995): 289-300.
Berkey CS, Hoaglin DC, Antczak-Bouckoms A, Mosteller F, Colditz GA. Meta-analysis of multiple outcomes by regression with random effects. Stat Med. Nov. 30, 1998;17(22):2537-50. doi: 10.1002/(sici)1097-0258(Nov. 30, 1998) 17:22<2537::aid-sim953>3.0.co;2-c. PMID: 9839346.
Mechtbauer, Wolfgang. "Conducting meta-analyses in R with the metafor package." Journal of statistical software 36.3 (2010): 1-48.
Marvel SW, Rotroff DM, Wagner MJ, Buse JB, Havener TM, McLeod HL, Motsinger-Reif AA; The ACCORD/ACCORDion Investigators. Common and rare genetic markers of lipid variation in subjects with type 2 diabetes from the ACCORD clinical trial. PeerJ. May 2, 2017;5:e3187. doi: 10.7717/peerj.3187. PMID: 28480134; PMCID: PMC5417062.
Rotroff DM, Yee SW, Zhou K, Marvel SW, Shah HS, Jack JR, Havener TM, Hedderson MM, Kubo M, Herman MA, Gao H, Mychaleckyi JC, McLeod HL, Doria A, Giacomini KM, Pearson ER, Wagner MJ, Buse JB, Motsinger-Reif AA; MetGen Investigators; ACCORD/ACCORDion Investigators. Genetic Variants in CPA6 and PRPF31 Are Associated With Variation in Response to Metformin in Individuals With Type 2 Diabetes. Diabetes. Jul. 2018;67(7):1428-1440. doi: 10.2337/db17-1164. Epub Apr. 12, 2018. PMID: 29650774; PMCID: PMC6014560.
Marees AT, de Kluiver H, Stringer S, Vorspan F, Curis E, Marie-Claire C, Derks EM. A tutorial on conducting genome-wide association studies: Quality control and statistical analysis. Int J Methods Psychiatr Res. Jun. 2018;27(2):e1608. doi: 10.1002/mpr.1608. Epub Feb. 27, 2018. PMID: 29484742; PMCID: PMC6001694.
Tibshirani, Robert. "Regression shrinkage and selection via the lasso." Journal of the Royal Statistical Society: Series B (Methodological) 58.1 (1996): 267-288.
Breiman, Leo. "Random forests." Machine learning 45.1 (2001): 5-32.
Chen, Tianqi, and Carlos Guestrin. "Xgboost: A scalable tree boosting system." Proceedings of the 22nd acm sigkdd International conference on knowledge discovery and data mining. 2016.
Fang H, Knezevic B, Burnham KL, Knight JC. XGR software for enhanced interpretation of genomic summary data, Illustrated by application to immunological traits. Genome Med. Dec. 13, 2016;8(1):129. doi: 10.1186/s13073-016-0384-y. PMID: 27964755; PMCID: PMC5154134.
The Gene Ontology Consortium. The Gene Ontology Resource: 20 years and still GOing strong. Nucleic Acids Res. Jan. 8, 2019;47(D1):D330-D338. doi: 10.1093/nar/gky1055. PMID: 30395331; PMCID: PMC6323945.
Grossmann S, Bauer S, Robinson PN, Vingron M. Improved detection of overrepresentation of Gene-Ontology annotations with par-

(56) References Cited

OTHER PUBLICATIONS ent child analysis. Bioinformatics. Nov. 15, 2007;23(22):3024-31. doi: 10.1093/bioinformatics/btm440. Epub Sep. 11, 2007. PMID: 17848398.
Fisher R, Pusztai L, Swanton C. Cancer heterogeneity: implications for targeted therapeutics. Br J Cancer. Feb. 19, 2013;108(3):479-85. doi: 10.1038/bjc.2012.581. Epub Jan. 8, 2013. PMID: 23299535; PMCID: PMC3593543.
Ryan J, Fransquet P, Wrigglesworth J, Lacaze P. Phenotypic Heterogeneity in Dementia: A Challenge for Epidemiology and Biomarker Studies. Front Public Health. Jun. 19, 2018;6:181. doi: 10.3389/fpubh.2018.00181. PMID: 29971228; PMCID: PMC6018385.
Manchia M, Cullis J, Turecki G, Rouleau GA, Uher R, Alda M. The impact of phenotypic and genetic heterogeneity on results of genome wide association studies of complex diseases. PLoS One. Oct. 11, 2013;8(10):e76295. doi: 10.1371/journal.pone.0076295. PMID: 24146854; PMCID: PMC3795757.
Nahta R, Esteva FJ. Herceptin: mechanisms of action and resistance. Cancer Lett. Feb. 8, 2006;232(2):123-38. doi: 10.1016/j.canlet.2005.01.041. PMID: 16458110.
Riddle MC. Effects of intensive glucose lowering in the management of patients with type 2 diabetes mellitus in the Action to Control Cardiovascular Risk in Diabetes (ACCORD) trial. Circulation. Aug. 24, 2010;122(8):844-6. doi: 10.1161/CIRCULATIONAHA.110.960138. PMID: 20733112; PMCID: PMC2980502.
Aquizerat BE, Vittinghoff E, Musone SL, Pawlikowska L, Kwok PY, Olgin JE, Tseng Zh. GWAS for discovery and replication of genetic loci associated with sudden cardiac arrest in patients with coronary artery disease. BMC Cardiovasc Disord. Jun. 10, 2011;11:29. doi: 10.1186/1471-2261-11-29. PMID: 21658281; PMCID: PMC3141757.
Glessner JT, Li J, Desai A, Palmer M, Kim D, Lucas AM, Chang X, Connolly JJ, Almoguera B, Harley JB, Jarvik GP, Ritchie MD, Sleiman PMA, Roden DM, Crosslin D, Hakonarson H. CNV Association of Diverse Clinical Phenotypes from eMERGE reveals novel disease biology underlying cardiovascular disease. Int J Cardiol. Jan. 1, 2020;298:107-113. doi: 10.1016/j.ijcard.2019.07.058. Epub Jul. 19, 2019. PMID: 31447229.
Hankir MK, Kranz M, Gnad T, Weiner J, Wagner S, Deuther-Conrad W, Bronisch F, Steinhoff K, Luthardt J, Kloting N, Hesse S, Seibyl JP, Sabri O, Heiker JT, Blüher M, Pfeifer A, Brust P, Fenske WK. A novel thermoregulatory role for PDE10A in mouse and human adipocytes. EMBO Mol Med. Jul. 1, 2016;8(7):796-812. doi: 10.15252/emmm.201506085. PMID: 27247380; PMCID: PMC4931292.
Nawrocki AR, Rodriguez CG, Toolan DM, Price O, Henry M, Forrest G, Szeto D, Keohane CA, Pan Y, Smith KM, Raheem IT, Cox CD, Hwa J, Renger JJ, Smith SM. Genetic deletion and pharmacological inhibition of phosphodiesterase 10A protects mice from diet-induced obesity and insulin resistance. Diabetes. Jan. 2014;63(1):300-11. doi: 10.2337/db13-0247. Epub Oct. 7, 2013. PMID: 24101672.
Cantin LD, Magnuson S, Gunn D, Barucci N, Breuhaus M, Bullock WH, Burke J, Claus TH, Daly M, Decarr L, Gore-Willse A, Hoover-Litty H, Kumarasinghe ES, Li Y, Liang SX, Livingston JN, Lowinger T, Macdougall M, Ogutu HO, Olague A, Ott-Morgan R, Schoenleber RW, Tersteegen A, Wickens P, Zhang Z, Zhu J, Zhu L, Sweet LJ. PDE-10A Inhibitors as insulin secretagogues. Bioorg Med Chem Lett. May 15, 2007;17(10):2869-73. doi: 10.1016/j.bmcl.2007.02.061. Epub Feb. 25, 2007. PMID: 17400452.
Loh K, Zhang L, Brandon A, Wang Q, Begg D, Qi Y, Fu M, Kulkarni R, Teo J, Baldock P, Brüning JC, Cooney G, Neely GG, Herzog H. Insulin controls food intake and energy balance via NPY neurons. Mol Metab. Apr. 12, 2017;6(6):574-584. doi: 10.1016/j.molmet.2017.03.013. Erratum in: Mol Metab. Nov. 2017;6(11):1562. Neely, Greg [corrected to Neely, Greg G]. PMID: 28580287; PMCID: PMC5444095.
Yi M, Li H, Wu Z, Yan J, Liu Q, Ou C, Chen M. A Promising Therapeutic Target for Metabolic Diseases: Neuropeptide Y Receptors in Humans. Cell Physiol Biochem. 2018;45(1):88-107. doi: 10.1159/000486225. Epub Dec. 22, 2017. PMID: 29310113.

Moonat S, Starkman BG, Sakharkar A, Pandey SC. Neuroscience of alcoholism: molecular and cellular mechanisms. Cell Mol Life Sci. Jan. 2010;67(1):73-88. doi: 10.1007/s00018-009-0135-y. Epub Sep. 10, 2009. PMID: 19756388; PMCID: PMC3747955.
Hwang BH, Suzuki R, Lumeng L, Li TK, McBride WJ. Innate differences in neuropeptide Y (NPY) mRNA expression in discrete brain regions between alcohol-preferring (P) and -nonpreferring (NP) rats: a significantly low level of NPY mRNA in dentate gyrus of the hippocampus and absence of NPY mRNA in the medial habenular nucleus of P rats. Neuropeptides. Dec. 2004;38(6):359-68. doi: 10.1016/j.npep.2004.09.004. PMID: 15567472.
Baldock PA, Allison SJ, Lundberg P, Lee NJ, Slack K, Lin EJ, Enriquez RF, McDonald MM, Zhang L, During MJ, Little DG, Eisman JA, Gardiner EM, Yulyaningsih E, Lin S, Sainsbury A, Herzog H. Novel role of Y1 receptors in the coordinated regulation of bone and energy homeostasis. J Biol Chem. Jun. 29, 2007;282(26):19092-102. doi: 10.1074/jbc.M700644200. Epub May 9, 2007. PMID: 17491016.
Nguyen AD, Mitchell NF, Lin S, Macia L, Yulyaningsih E, Baldock PA, Enriquez RF, Zhang L, Shi YC, Zolotukhin S, Herzog H, Sainsbury A. Y1 and Y5 receptors are both required for the regulation of food intake and energy homeostasis in mice. PLoS One. 2012;7(6):e40191. doi: 10.1371/journal.pone.0040191. Epub Jun. 29, 2012. PMID: 22768253; PMCID: PMC3387009.
Mychaleckyj JC, Farber EA, Chmielewski J, Artale J, Light LS, Bowden DW, Hou X, Marcovina SM. Buffy coat specimens remain viable as a DNA source for highly multiplexed genome-wide genetic tests after long term storage. J Transl Med. Jun. 10, 2011,9:91. doi: 10.1186/1479-5876-9-91. PMID: 21663644; PMCID: PMC3128059.
Niennattrakul, Vit, and Chotirat Ann Ratanamahatana. "Shape averaging under time warping." 2009 6th International Conference on Electrical Engineering/Electronics, Computer, Telecommunications and Information Technology. vol. 2. IEEE, 2009.
Gerstein HC, Action to Control Cardiovascular Risk in Diabetes Study Group, Miller ME, Byington RP, Goff DC Jr, Bigger JT, Buse JB, Cushman WC, Genuth S, Ismail-Beigi F, Grimm RH Jr, Probstfield JL, Simons-Morton DG, Friedewald WT. Effects of intensive glucose lowering in type 2 diabetes. N Engl J Med. Jun. 12, 2008;358(24):2545-59. doi: 10.1056/NEJMoa0802743. Epub Jun. 6, 2008. PMID: 18539917; PMCID: PMC4551392.
Garber et al., "Consensus Statement by the American Association of Clinical Endocrinologists and American College of Endocrinology on the Comprehensive Type 2 Diabetes Management Algorithm—2019 Executive Summary", Endocrine Practice vol. 25 No. Jan. 1, 2019.
American Diabetes Association. 6. Glycemic Targets: Standards of Medical Care in Diabetes—2019. Diabetes Care. Jan. 2019;42(Suppl 1):S61-S70. doi: 10.2337/dc19-S006. PMID: 30559232.
Genuth S, Ismail-Beigi F. Clinical implications of the Accord trial. J Clin Endocrinol Metab. Jan. 2012;97(1):41-8. doi: 10.1210/jc.2011-1679. Epub Nov. 2, 2011. PMID: 22049171.
Shah HS, Gao H, Morieri ML, Skupien J, Marvel S, Paré G, Mannino GC, Buranasupkajorn P, Mendonca C, Hastings T, Marcovina SM, Sigal RJ, Gerstein HC, Wagner MJ, Motsinger-Reif AA, Buse JB, Kraft P, Mychaleckyj JC, Doria A. Genetic Predictors of Cardiovascular Mortality During Intensive Glycemic Control in Type 2 Diabetes: Findings From the ACCORD Clinical Trial. Diabetes Care. Nov. 2016;39(11):1915-1924. doi: 10.2337/dc16-0285. Epub Aug. 15, 2016. PMID: 27527847; PMCID: PMC5079609.
Basu S, Raghavan S, Wexler DJ, Berkowitz SA. Characteristics Associated With Decreased or Increased Mortality Risk From Glycemic Therapy Among Patients With Type 2 Diabetes and High Cardiovascular Risk: Machine Learning Analysis of the ACCORD Trial. Diabetes Care. Mar. 2018,41(3):604-612. doi: 10.2337/dc17-2252. Epub Dec. 26, 2017. PMID: 29279299; PMCID: PMC5829969.
Hempe JM, Liu S, Myers L, McCarter RJ, Buse JB, Fonseca V. The hemoglobin glycation index identifies subpopulations with harms or benefits from intensive treatment in the Accord trial. Diabetes Care. Jun. 2015;38(6):1067-74. doi: 10.2337/dc14-1844. Epub Apr. 17, 2015. PMID: 25887355; PMCID: PMC4439529.
Riddle MC, Ambrosius WT, Brillon DJ, Buse JB, Byington RP, Cohen RM, Goff DC JR, Malozowski S, Margolis KL, Probstfield

(56) References Cited

OTHER PUBLICATIONS

JL, Schnall A, Seaquist ER; Action to Control Cardiovascular Risk in Diabetes Investigators. Epidemiologic relationships between A1C and all-cause mortality during a median 3.4-year follow-up of glycemic treatment in the Accord trial. Diabetes Care. May 2010;33(5):983-90. doi: 10.2337/dc09-1278. PMID: 20427682; PMCID: PMC2858202.

Riddle MC, Karl DM. Individualizing targets and tactics for high-risk patients with type 2 diabetes: practical lessons from Accord and other cardiovascular trials. Diabetes Care. Oct. 2012;35(10):2100-7. doi: 10.2337/dc12-0650. PMID: 22996182; PMCID: PMC3447843.

Duckworth W, Abraira C, Moritz T, Reda D, Emanuele N, Reaven PD, Zieve FJ, Marks J, Davis SN, Hayward R, Warren SR, Goldman S, McCarren M, Vitek ME, Henderson WG, Huang GD; VADT Investigators. Glucose control and vascular complications in veterans with type 2 diabetes. N Engl J Med. Jan. 8, 2009;360(2):129-39. doi: 10.1056/NEJMoa0808431. Epub Dec. 17, 2008. Erratum in: N Engl J Med. Sep. 3, 2009;361(10):1028. Erratum in: N Engl J Med. Sep. 3, 2009;361(10):1024-5. PMID: 19092145.

Reaven PD, Emanuele NV, Wiitala WL, Bahn GD, Reda DJ, McCarren M, Duckworth WC, Hayward RA; VADT Investigators. Intensive Glucose Control in Patients with Type 2 Diabetes—15-Year Follow-up. N Engl J Med. Jun. 6, 2019;380(23):2215-2224. doi: 10.1056/NEJMoa1806802. PMID: 31167051; PMCID: PMC6706253.

Mai Y, Patel HR, Hawkins EJ, Doliba NM, Matschinsky FM, Ahima RS. Insulin secretion is increased in pancreatic slets of neuropeptide Y-deficient mice. Endocrinology. Dec. 2007;148(12):5716-23. doi: 10.1210/en.2007-0404. Epub Aug. 23, 2007. PMID: 17717054.

Thiele TE, Koh MT, Pedrazzini T. Voluntary alcohol consumption is controlled via the neuropeptide Y Y1 receptor. J Neurosci. Feb. 1, 2002;22(3):RC208. doi: 10.1523/JNEUROSCI.22-03-j0006. 2002. PMID: 11826154; PMCID: PMC6758511.

Liu et al., "Association studies of up to 1.2 million individuals yield new insights into the genetic etiology of tobacco and alcohol use", Nat Geriet Feb. 2019; 51(2): 237-244. doi:10.1038/s41588-018-0307-5.

Keogh, Eamonn J., and Michael J. Pazzani. "Scaling up dynamic time warping to massive datasets." European Conference on Principles of Data Mining and Knowledge Discovery. Springer, Berlin, Heidelberg, 1999.

Galili T. dendextend: an R package for visualizing, adjusting and comparing trees of hierarchical clustering. Bioinformatics. Nov. 15, 2015;31(22):3718-20. doi: 10.1093/bioinformatics/btv428. Epub Jul. 23, 2015. PMID: 26209431; PMCID: PMC4817050.

Riley RD, Price MJ, Jackson D, Wardle M, Gueyffier F, Wang J, Staessen JA, White IR. Multivariate meta-analysis using individual participant data. Res Synth Methods. Jun. 2015;6(2):157-74. doi: 10.1002/jrsm.1129. Epub Nov. 21, 2014. PMID: 26099484; PMCID: PMC4847645.

\* cited by examiner

IDENTIFYING PATIENTS FOR INTENSIVE HYPERGLYCEMIA MANAGEMENT

RELATED APPLICATIONS

This application claims priority from U.S. Provisional Application No. 62/982,195, filed 27 Feb. 2020, the subject matter of which is incorporated herein by reference in its entirety.

STATEMENT REGARDING GOVERNMENT RIGHTS

This invention was made with government support under TR002547 awarded by the National Institutes of Health. The government has certain rights in this invention.

TECHNICAL FIELD

This invention relates to medical diagnostic systems, and more particularly, to a predictive model for identifying patients for whom intensive hyperglycemia management is appropriate.

BACKGROUND

The Action to Control Cardiovascular Risk in Diabetes (ACCORD) was a landmark trial to examine the effect of intensively treating glycemia, targeting maintenance of a level of glycated hemoglobin A1c (HbA1c) at less than six percent, versus more modest therapy targeting an HbA1c level between seven and seven and nine-tenths percent. The study was conducted in patients with type 2 diabetes at high cardiovascular risk with a primary endpoint of time to first occurrence of major adverse cardiovascular events (MACE), specifically non-fatal myocardial infarction, non-fatal stroke, or cardiovascular death. Notably, the intensive glycemia arm of the trial was terminated prematurely due to an increase in cardiovascular and overall mortality. The findings from ACCORD have had important implications regarding guidelines for glycemic management.

SUMMARY OF THE INVENTION

In accordance with one aspect of the invention, a method for assigning a treatment to a patient is provided. A set of genetic data representing a patient. A polygenic score representing the likelihood that a patient will benefit from intensive glycemia treatment is generated from the set of genetic data. A parameter representing a response of the patient to intensive glycemia treatment is assigned according to the polygenic score.

In accordance with another aspect of the present invention, a system includes a processor and a computer readable medium that stores executable instructions for assigning a treatment to a patient. The executable instructions include a network interface that receives a set of genetic data representing a patient and a feature extractor that generates a polygenic score representing the likelihood that a patient belongs to a treatment class likely to benefit from intensive glycemia treatment given the set of genetic data. A predictive model assigns a parameter to the patient representing the response of the patient to intensive glycemia treatment according to the polygenic score and a set of clinical parameters representing the patient.

In accordance with a further aspect of the invention, a method is provided for assigning a treatment to a patient. A set of genetic data representing a patient is received, and a polygenic score representing the likelihood that a patient belongs to a treatment class likely to benefit from intensive glycemia treatment given the set of genetic data is generated. The patient is assigned to one of a plurality of treatment classes according to the polygenic score and a set of clinical parameters representing the patient. The plurality of treatment classes include the treatment class likely to benefit from intensive glycemia treatment. Intensive glycemia treatment is provided to the patient if the patient is assigned to the treatment class likely to benefit from intensive glycemia treatment.

DETAILED DESCRIPTION

"Intensive glycemia treatment", as used herein, refers to clinical treatment of a patient that targets a Hemoglobin A1c (HbA1c) score below 6%. Intensive glycemia treatment can include, but does not necessarily include, treatment of a patient with metformin, sulfonylureas, thiazolidinediones, and/or insulin or hyperglycemia medications.

A "predictive model," as used herein, is a statistical or machine learning model that generates a parameter representing a patient based on a series of inputs representing the patient.

Figure 1:
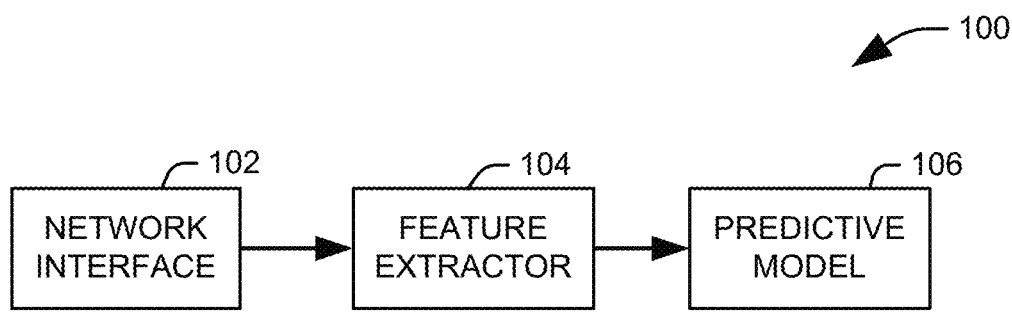
FIG. 1 illustrates a system for assigning a parameter to a patient representing the expected response of the patient to intensive glycemia treatment.

FIG. 1 illustrates a system 100 for assigning a parameter to a patient representing the expected response of the patient to intensive glycemia treatment. It will be appreciated that the system 100 can be implemented as software instructions executed by one or more associated processors, firmware running on a medical device, dedicated hardware, such as an application specific integrated circuit or a field programmable gate array, or as some combination of these methods. The inventors have identified a genetic subtype of type 2 diabetes that benefits from intensive glycemia treatment even where intensive glycemia treatment has been contraindicated for the larger population. The system 100 evaluates the likelihood that the patient belongs to this genetic subtype using genetic factors, and in some implementations, a combination of genetic and clinical factors.

To this end, the system 100 includes a network interface 102 that receives a set of genetic data representing a patient. In one implementation, the set of genetic data includes a series of parameters representing a set of single nucleotide polymorphisms (SNPs). For example, the set of SNPs include SNPs in Mas1 proto-oncogene (MAS1), Neural EGFL Like 1 (NELL1), and Supervillin (SVIL), and can include rs220721. Where clinical parameters are used by the system, some or all of the clinical parameters can be retrieved from an electronic health records system (not shown) or a local sensor system (not shown) via the network interface 102.

A feature extractor 104 generates a polygenic score representing the likelihood that a patient belongs to a treatment class likely to benefit from intensive glycemia treatment from the set of genetic data. A "polygenic score," as used herein, is a numerical score representing an aggregation of risk of a given condition conferred by multiple genetic variants, or single nucleotide polymorphisms (SNPs). In one implementation, the various SNPs from the set of genetic data each have an associated weight representing the strength of their association with a positive response to intensive glycemia treatment (e.g., as log odds ratios obtained from training data). The polygenic score can then be calculated for each individual by summing the weighted risk values for the SNPs present in the patient's genetic data.

In one implementation, the feature extractor 104 can determine categorical and continuous parameters representing clinical values such as a blood pressure of the patient (e.g., mean arterial pressure, diastolic blood pressure, systolic blood pressure), a measured of blood concentration of thyroid stimulating hormone for the patient, and alcohol consumption by the patient. In one example, the parameters can include descriptive statistics, such as measures of central tendency (e.g., median, mode, arithmetic mean, or geometric mean) and measures of deviation (e.g., range, interquartile range, variance, standard deviation, etc.) of time series of the clinical parameter. Additionally or alternatively, the monitored clinical parameters and the genetic data can be used to assign a plurality of categorical parameters to the patient according to various rule sets, for example, representing the presence or absence of a given condition or behavior.

The predictive model 106 can utilize one or more pattern recognition algorithms, each of which analyzes the polygenic score and any provided clinical parameters to assign a continuous or categorical parameter to the user. In one example, the predictive model 106 can assign a continuous parameter that corresponds to the likelihood that the patient will respond to a specific treatment (e.g., metformin, sulfonylureas, thiazolidinediones, or insulin or hyperglycemia medications) or intensive glycemia treatment generally. Alternatively, the predictive model 106 can assign a categorical parameter that corresponds to a recommended specific treatment or a recommendation for or against intensive glycemia treatment, or alternatively, to ranges of likelihoods that the patient will respond to a specific treatment or to intensive glycemia treatment generally.

Where multiple classification or regression models are used, an arbitration element can be utilized to provide a coherent result from the plurality of models. The training process of a given classifier will vary with its implementation, but training generally involves a statistical aggregation of training data into one or more parameters associated with the output class. For rule-based models, such as decision trees, domain knowledge, for example, as provided by one or more human experts, can be used in place of or to supplement training data in selecting rules for classifying a user using the extracted features. Any of a variety of techniques can be utilized for the classification algorithm, including support vector machines, regression models, self-organized maps, fuzzy logic systems, data fusion processes, boosting and bagging methods, rule-based systems, or artificial neural networks.

For example, a support vector machine (SVM) classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. In one implementation, the SVM can be implemented via a kernel method using a linear or non-linear kernel.

An artificial neural network (ANN) classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

Many ANN classifiers are fully-connected and feedforward. A convolutional neural network, however, includes convolutional layers in which nodes from a previous layer are only connected to a subset of the nodes in the convolutional layer. Recurrent neural networks are a class of neural networks in which connections between nodes form a directed graph along a temporal sequence. Unlike a feedforward network, recurrent neural networks can incorporate feedback from states caused by earlier inputs, such that an output of the recurrent neural network for a given input can be a function of not only the input but one or more previous inputs. As an example, Long Short-Term Memory (LSTM) networks are a modified version of recurrent neural networks, which makes it easier to remember past data in memory.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used. The output of the predictive model 106 can then be provided to a user or stored in a non-transitory computer readable medium for later retrieval.

Figure 2:
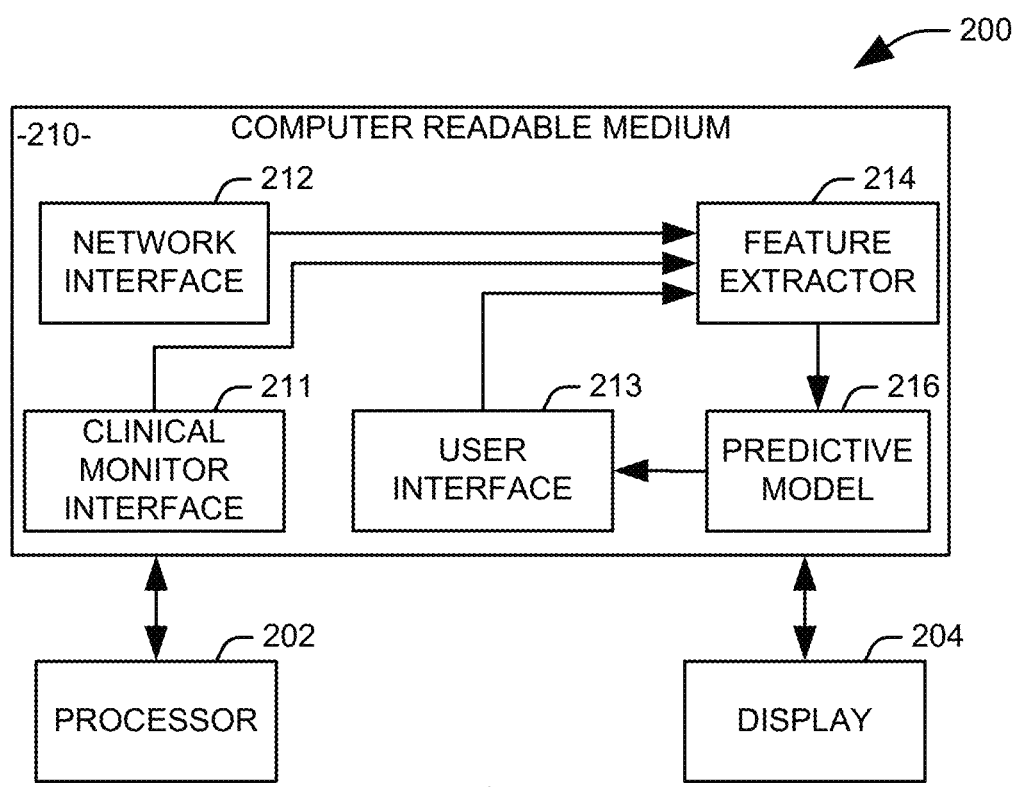
FIG. 2 illustrates an example of a system implementing a model for identifying patients for whom intensive hyperglycemic management is appropriate.
Figure 3:
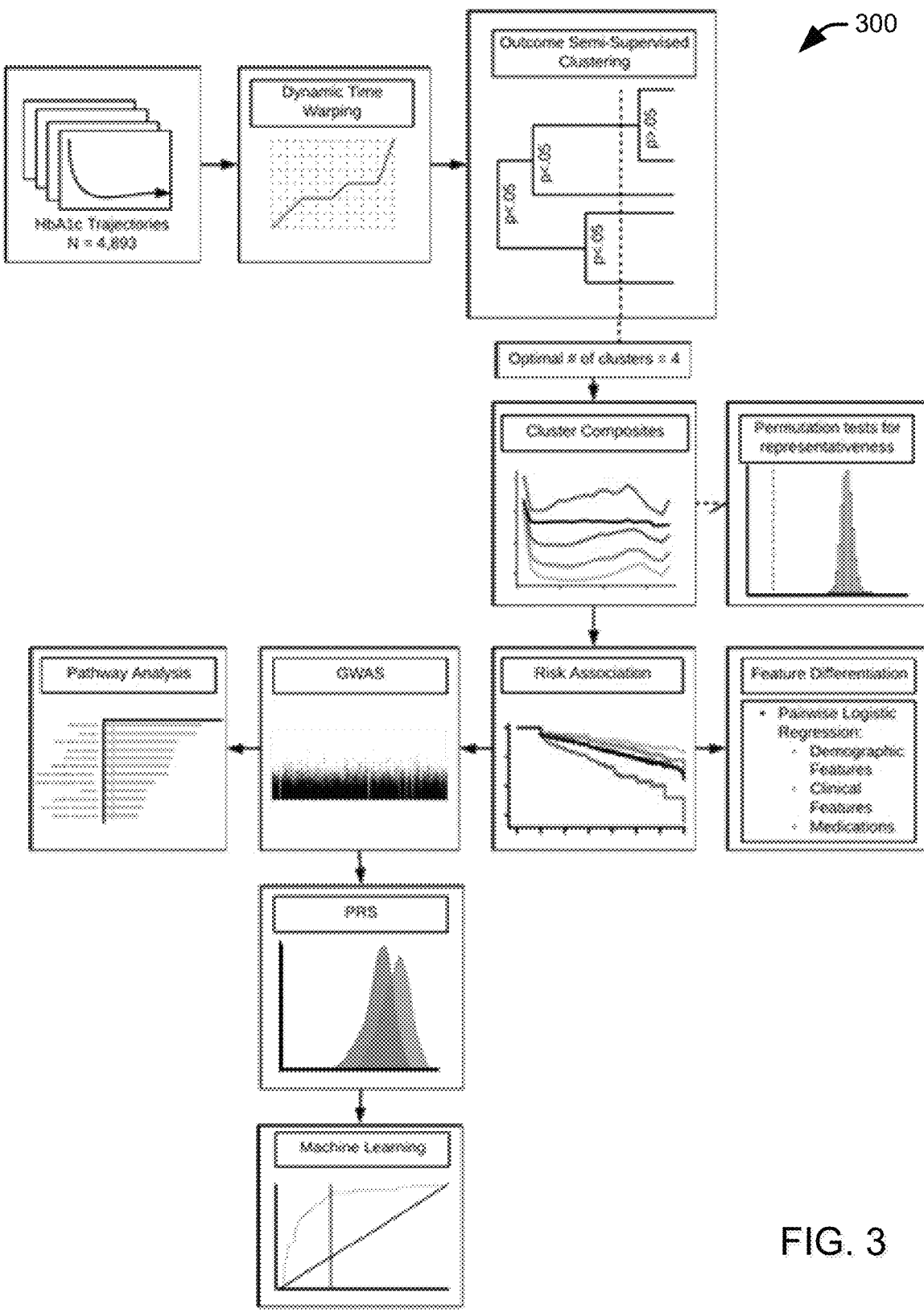
FIG. 3 illustrates a workflow describing the process of identifying clusters using dynamic time warping, performing the genomics studies, and developing the risk model used in one implementation of the system of FIG. 2.

FIG. 2 illustrates one example of a system 200 for selecting a treatment for type 2 diabetes for a patient. FIG. 3 illustrates a workflow 300 describing the process of identifying clusters using dynamic time warping, performing the genomics studies, and developing the risk model used in one implementation of the system 200 of FIG. 2. Current management of type 2 diabetes includes a relative contraindication to intensive hyperglycemia management in patients at high cardiovascular disease risk. This guidance is partially motivated by evidence of harms in the ACCORD trial. In the ACCORD trial, individuals with type 2 diabetes and either a history of cardiovascular disease or two or more risk factors for cardiovascular disease were randomly assigned to receive standard glycemic treatment, targeting an HbA1c between 7% and 7.9% or intensive glycemia treatment, targeting an HbA1c below 6%. Patients were then further randomized to determine whether intensively treating blood pressure or dyslipidemia was effective at reducing MACE. Trial outcomes included first occurrence of MACE (i.e., non-fatal heart attack, non-fatal stroke, or cardiovascular death), mortality from any cause, mortality due to cardiovascular diseases, congestive heart failure, nonfatal myocardial infarction, nonfatal stroke, total stroke, expanded macrovascular events, and coronary heart disease.

Although there was a significant increase in mortality in the intensive glycemia arm of the ACCORD trial, heterogeneity was observed. Previous studies have demonstrated that individuals at greatest risk of mortality and MACE were those intensively treated that were unable to reach the intensive HbA1c target. In addition to ACCORD, two other trials, the Veterans Affairs Diabetes Trial (VADT) and Action in Diabetes and Vascular Disease: Preterax and Diamicron Modified Release Controlled Evaluation (ADVANCE), investigated whether intensive glycemia modified outcomes in patients with advanced type 2 diabetes, and both failed to find benefit in CVD related outcomes.

In designing and training the system, dynamic time warping was applied to measure the similarity between patient HbA1c trajectories while enrolled in ACCORD and cluster these patients into subgroups based on their HbA1c trajectories. In doing so, a subgroup of patients intensively treated in ACCORD that had a significantly lower risk of mortality and MACE than patients receiving standard glycemic treatment was identified. This analysis was paired with a genome-wide association study to identify genetic variants associated with membership in this low-risk group, and a polygenic score was constructed using genetic variants and baseline clinical factors to predict patients likely to benefit from intensive intervention.

Figures 4A, 4B, 4C, 4D:
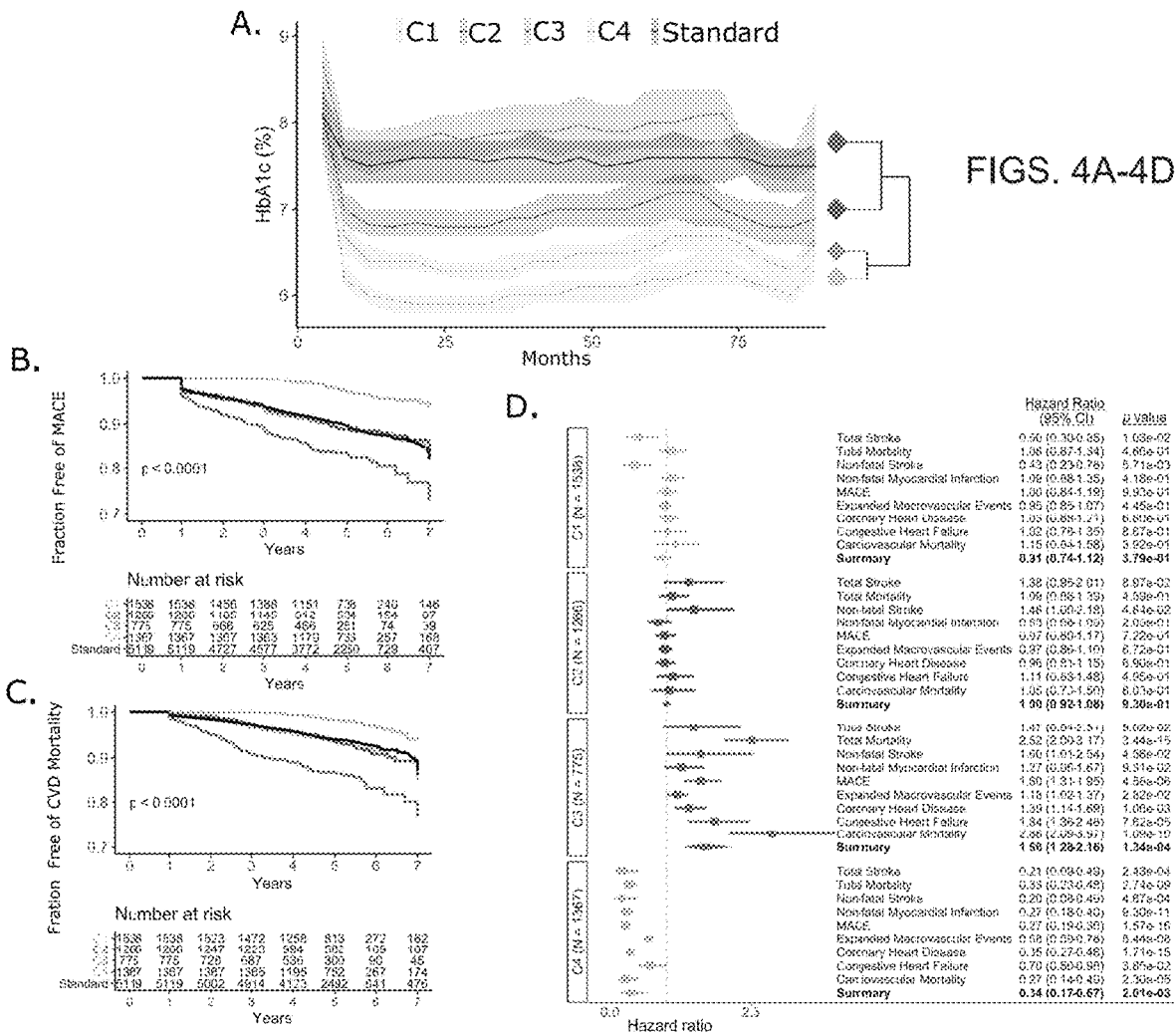
FIG. 4(A) illustrates the composite trajectories from each of the four clusters based on HbA1c trajectories compared to the composite trajectory from the standard arm of the ACCORD trial (S)
FIG. 4(B) illustrates Kaplan Meier curves of each cluster and standard treatment for developing the major adverse cardiovascular events (MACE)—a non-fatal heart attack, non-fatal stroke, or cardiovascular death.
FIG. 4(C) illustrates Kaplan Meier curves of each cluster and standard treatment for developing the cardiovascular disease (CVD) mortality.
FIG. 4(D) is a forest plot of hazard ratios for each CVD outcome separated by clusters relative to standard glycemia treatment.

The dynamic time warping algorithm was used to calculate the dissimilarity for each pairwise combination of patient HbA1c trajectories randomized to receive intensive glycemia treatment. The dynamic time warping algorithm calculates the Euclidian distance between each combination of points along a trajectory, creating an M×N matrix, where M is the number of points in one trajectory and N is the number of points in the second trajectory. The minimum cost is determined from the optimal path in the M×N matrix. Unsupervised hierarchical clustering with Ward's method was used to cluster patient HbA1c trajectories based on dynamic time warping dissimilarity. Each parent cluster in the resulting dendrogram was iteratively cut to form two child clusters, which were tested for associations with outcomes using a Gox proportional hazards model, until further splits produced insignificant differences between child clusters. For each cluster, composite trajectories were created by averaging the HbA1c values across all individuals at each time point within the cluster. FIG. 4(A) illustrates the composite trajectories from each of the four clusters based on HbA1c trajectories compared to the composite trajectory from the standard arm of the ACCORD trial (S). The interval surrounding the composite HbA1c trajectory represents two median absolute deviations.

Based on the stopping criteria described above, four distinct clusters were identified. The characterization of each cluster regarding outcome incidence, sex, race, and other factors are provided in Table 1.

TABLE 1

| | Intensive arm (N = 4,946) | | | | | |
|---|---|---|---|---|---|---|
| | All Clinical Groups | Clinical Group 1 (C1) (N = 1538) | Clinical Group 2 (C2) (N = 1266) | Clinical Group 3 (C3) (N = 775) | Clinical Group 4 (C4) (N = 1367) | Standard arm (N = 5,119) |
| MACE[1] | 470 (9.50) | 168 (10.92) | 135 (10.66) | 125 (16.13) | 42 (3.07) | 543 (10.61) |
| Cardiovascular mortality | 159 (3.21) | 53 (3.45) | 38 (3.00) | 57 (7.35) | 11 (0.80) | 144 (2.81) |
| Total mortality[2] | 338 (6.83) | 114 (7.41) | 86 (6.79) | 106 (13.68) | 32 (2.34) | 327 (6.39) |
| Congestive heart failure[3] | 226 (4.57) | 67 (4.36) | 61 (4.82) | 57 (7.35) | 41 (3.00) | 212 (4.14) |
| Non-fatal myocardial infarction[3] | 281 (5.68) | 115 (7.48) | 76 (6.00) | 63 (8.13) | 27 (1.98) | 344 (6.72) |
| Non-fatal stroke[3] | 77 (1.56) | 12 (0.78) | 36 (2.84) | 24 (3.10) | 5 (0.37) | 94 (1.84) |
| Total stroke[4] | 85 (1.71) | 16 (1.04) | 38 (3.00) | 25 (3.23) | 6 (0.44) | 106 (2.07) |
| Expanded macrovascular events | 1115 (22.54) | 363 (23.60) | 304 (24.01) | 210 (27.10) | 238 (17.41) | 1229 (24.00) |
| Coronary heart disease[3] | 547 (11.06) | 201 (13.07) | 155 (12.24) | 126 (16.26) | 65 (4.75) | 627 (12.25) |
| Race | | | | | | |
| White | 3093 (62.54) | 979 (67.55) | 751 (56.80) | 365 (47.70) | 998 (71.92) | 3199 (62.49) |
| Other | 1853 (37.46) | 559 (32.45) | 515 (43.20) | 410 (52.30) | 369 (28.08) | 1920 (37.50) |
| Gender | | | | | | |
| Female | 1903 (38.48) | 557 (37.97) | 498 (39.40) | 354 (47.70) | 494 (32.09) | 1966 (38.41) |
| Male | 3043 (61.52) | 981 (62.03) | 768 (60.60) | 421 (52.30) | 873 (67.91) | 3153 (61.59) |
| Blood pressure arm | | | | | | |
| Intensive BP | 1128 (22.81) | 352 (22.89) | 275 (21.72) | 203 (26.19) | 298 (21.80) | 1183 (23.11) |
| Lipid Fibrate | 1323 (26.75) | 410 (26.66) | 357 (28.20) | 179 (23.10) | 377 (27.58) | 1390 (27.15) |
| Lipid Placebo | 1340 (27.09) | 427 (27.76) | 315 (24.88) | 193 (24.90) | 405 (29.63) | 1369 (26.74) |
| Standard BP | 1155 (23.25) | 349 (22.60) | 319 (25.20) | 200 (25.81) | 287 (20.99) | 1177 (23.00) |
| Baseline cardiovascular risk | 1751 (35.40) | 527 (34.27) | 473 (37.36) | 330 (42.58) | 421 (30.80) | 1782 (34.81) |
| Baseline HbA1c % (mean ± sd) | 8.27 ± 1.01 | 8.13 ± 0.94 | 8.34 ± 1.00 | 8.86 ± 0.99 | 8.04 ± 0.98 | 8.29 ± 1.00 |
| Baseline Age, years (mean ± sd) | 62.73 ± 6.63 | 63.23 ± 6.64 | 62.60 ± 6.57 | 61.97 ± 7.12 | 62.73 ± 6.33 | 62.72 ± 6.60 |
| Baseline years with diabetes, years (mean ± sd) | 10.71 ± 7.55 | 10.44 ± 7.37 | 11.45 ± 7.41 | 13.77 ± 8.14 | 8.58 ± 6.82 | 10.85 ± 7.60 |
| Baseline diabetes medications (insulin excluded) | | | | | | |
| ≥1 | 4127 (83.44) | 1315 (85.50) | 1092 (86.26) | 585 (75.48) | 1135 (83.02) | 4248 (82.98) |
| ≥2 | 2495 (50.44) | 851 (55.33) | 713 (56.32) | 352 (45.42) | 579 (42.36) | 2554 (49.89) |
| ≥3 | 546 (11.04) | 206 (13.39) | 170 (13.43) | 59 (7.61) | 111 (8.12) | 557 (10.88) |
| Baseline insulin | 1686 (34.09) | 465 (30.23) | 472 (37.29) | 458 (59.10) | 291 (21.29) | 1831 (35.77) |

Permutation testing demonstrated that composite trajectories for Cluster 1 (C1), Cluster 2 (C2) and Cluster 4 (C4) were significantly representative of their underlying cluster member trajectories while the composite trajectory for Cluster 3 (C3) was not significantly different from randomly selected trajectories (P>0.05). The mean HbA1c at four months was lower for C1, C2, and C4, 6.59% and 7.16%, 6.19%, respectively, compared to 7.68% in the standard arm. C3 had highest mean of 8.05% HbA1c at four months.

The four identified clusters displayed different incidence rates for adverse outcomes. C4 displayed the lowest risk across multiple outcomes, MACE, and total mortality. C3 displayed the greatest risk for MACE and total mortality. Importantly, all intensive clusters had significantly increased risk of hypoglycemic events compared to the standard arm, even C4 which had lower risk of CVD related outcomes. Of the intensive clusters, C4 had the lowest rate of severe hypoglycemic events, whereas C3 had the greatest risk. Unlike C1 and C4, individuals in C2 and C3 that had a hypoglycemic event had their first event earlier, on average, than individuals in the standard arm. Meta-analysis across outcomes indicated that C4 had the overall lowest risk followed by C1. C3 had the greatest risk of adverse outcomes. FIG. 4(B) illustrates Kaplan Meier curves of each clinical group and standard treatment for developing the major adverse cardiovascular events (MACE)—a non-fatal heart attack, non-fatal stroke, or cardiovascular death. FIG. 4(C) illustrates Kaplan Meier curves of each clinical group and standard treatment for developing the cardiovascular disease (CVD) mortality. FIG. 4(D) is a forest plot of hazard ratios for each CVD outcome separated by clinical group relative to standard glycemia treatment. The summary hazard ratio is the meta-analysis of all outcomes in the cluster after accounting for covariance between outcomes.

Differences in clinical and demographic features were observed between clusters. C4 had a greater proportion of males and White individuals than the two high risk clusters, C3 and C2. C4 also had fewer years since their type 2 diabetes diagnosis. After adjusting for years with type 2 diabetes and increased alcohol intake, fewer eye diseases and depression at baseline were observed in C4. Individuals in C4 were also older when diagnosed with type 2 diabetes than individuals in C2 and C3. After adjusting for years with type 2 diabetes, compared to C1, individuals in C4 were less likely to use biguanides, sulfonylureas, and thiazolidinediones. C4 also had significantly lower proportions of individuals using insulin at baseline than C2 and C3. Essentially, the inventors have identified a genetic subtype of type 2 diabetes exists that is responsive to intensive glycemia treatment, despite the lack of efficacy observed across the overall cohort, and the system 200 identifies patients who are likely to belong to this subtype.

These findings point to the existence of a genetically distinct type 2 diabetes subtype (C4) that is responsive to intensive glycemia treatment. By incorporating a risk model that incorporates baseline clinical and genetic factors, the system 200 identifies patients in this subtype that are likely to benefit from intensive glycemia treatment. The system 200 includes a processor 202, a display 204, and a non-transitory computer readable medium 210 storing computer readable instructions, executed by the processor 202. The executable instructions stored on the non-transitory computer readable medium 210 include a clinical monitor interface 211 that can receive data from one or more monitoring systems tracking clinical parameters for the patient. Monitored clinical parameters can include heart rate, arterial blood pressure, respiratory rate, peripheral arterial oxyhemoglobin saturation, as measured by pulse oximetry, and temperature. It will be appreciated that a "clinical parameter," as used herein, can represent biometric parameters, demographics of the patient, such as age or sex, and behaviors, personal history, medication history, or medical history of the patient.

The executable instructions further include a network interface 212 via which the system 200 communicates with other systems (not shown) via a network connection, for example, an Internet connection, and/or a connection to an internal network. In the illustrated example, the other systems can include an electronic health records (EHR) system that stores medical information for the patient, and the network interface 212 can include an application program interface (API) (not shown) for communicating with the EHR system. Data retrieved from the EHR can include both clinical parameters for the patient as well as a set of genetic data for the patient. In one example, the set of genetic data is provided as genome-wide association study. It will be appreciated that, in some implementations, the monitoring systems can communicate with the system 200 via a local or wide-area network connection, and that, in this instance, the network interface 212 and the clinical monitor interface 211 may share some or all of their components. Further, where patient data is not available from the EHR, relevant information for the patient can be entered via an appropriate user interface 213.

Information retrieved via the clinical monitor interface 211 and the network interface 212 is provided to a feature extractor 215 that extracts a plurality of features for use at a predictive model 216. In the illustrated example, the feature extractor 215 uses the set of genetic data for the patient to generate a polygenic score representing the likelihood that the patient belongs to the cluster of patients who respond well to intensive glycemia treatment. In the illustrated example, single nucleotide polymorphisms (SNPs) associated with membership in the intensively treated cluster with lower risk of MACE (i.e., cluster 4) versus all other participants were initially identified using logistic regression, with a variable selection procedure used to address potential confounding using a backward selection approach and Bayesian information criteria. A principal component analysis was performed to address population substructure using and the first three principal components were forced into the model. These principal components, sex, years with diabetes, body mass index, and the use of sulfonylurea, biguanide, thiazolidinedione, or any type of insulin were included as covariates.

The results of this analysis were used to construct a polygenic score for use in a predictive model 216 to predict patients likely to belong to the cluster with lower risk of MACE and mortality. In the illustrated implementation, the polygenic score utilizes around 278,073 SNPs with specific weights. Members of cluster 4 had a lower mean PRS relative to the other clusters. In particular, rs220721, located in MAS1, was the most significantly associated with C4 membership. The T allele of rs220721 conferred a 1.38 fold increase in likelihood of C4 membership. Three genotyped SNPs—rs220721, rs1793004, and rs1270874 reached suggestive significance ($P<5\times10^{-6}$).

The MAS1 receptor is a constitutively active GPCR expressed in many tissues, and interacts with angiotensin-(1-7) (Ang(1-7)), a MAS1 agonist, and may play a role in ischemic stroke and CVD. Ang(1-7) regulates insulin secretion through a MAS-dependent cAMP signaling in pancreatic islet cells and reduces hyperglycemia in a rat model of T2D. Pharmacological antagonism and Mas$^{(-/-)}$ mice displayed significant reductions in insulin secretion suggesting a potential role for MAS1 in glycemic response. SNPs in MAS1 are in linkage disequilibrium with insulin-like growth factor 2 receptor (IGF2R), and genetic variation in IGF2R has been previously associated with coronary heart disease, and to impact circulating levels of IGF2R, which has been associated with T2D.

In another implementation, sets of SNPs were selected using a clumping procedure based on twenty-eight unique combinations of hyperparameters. Polygenic scores were derived based on each set of "clumped" variants, and each p value threshold (CT-PS). In addition, a penalized logistic regression framework was used to derive a Stacked Clumping and Thresholding Polygenic Score (SCT-PS). This approach generated multiple PS for each individual, and then penalized regression was used to derive an optimal combination of each PS, from which the weighted allele counts were summed to create the final SCT-PS to predict clinical group membership.

The feature extractor 215 can also extract clinical features representing the patient for use at the predictive model 216. In the illustrated implementation, the predictive model 216 uses a regression model to assign a score to a patient representing the patient's response to intensive hyperglycemic management and selects a treatment class according to the assigned score. In one example, the regression model can use the polygenic score as well as a metric representing the patient's blood pressure, a metric representing a measurement of a thyroid stimulating hormone of the patient, and a metric representing the patient's drinking behavior to generate the score for the patient. An appropriate treatment can then be selected for the patient according to the score assigned by the regression model. For example, where the patient is determined to be suitable for intensive hyperglycemic management, the treatment can include treatment with at least one of metformin, sulfonylureas, thiazolidinediones, and insulin products. If the patient is not determined to be a candidate for intensive hyperglycemic management, the patient can be treated with one of glucagon-like peptide-1 (GLP-1) receptor agonists and sodium-glucose co-transporter 2 (SGLT-2) inhibitors.

Figures 5A, 5B, 5C:
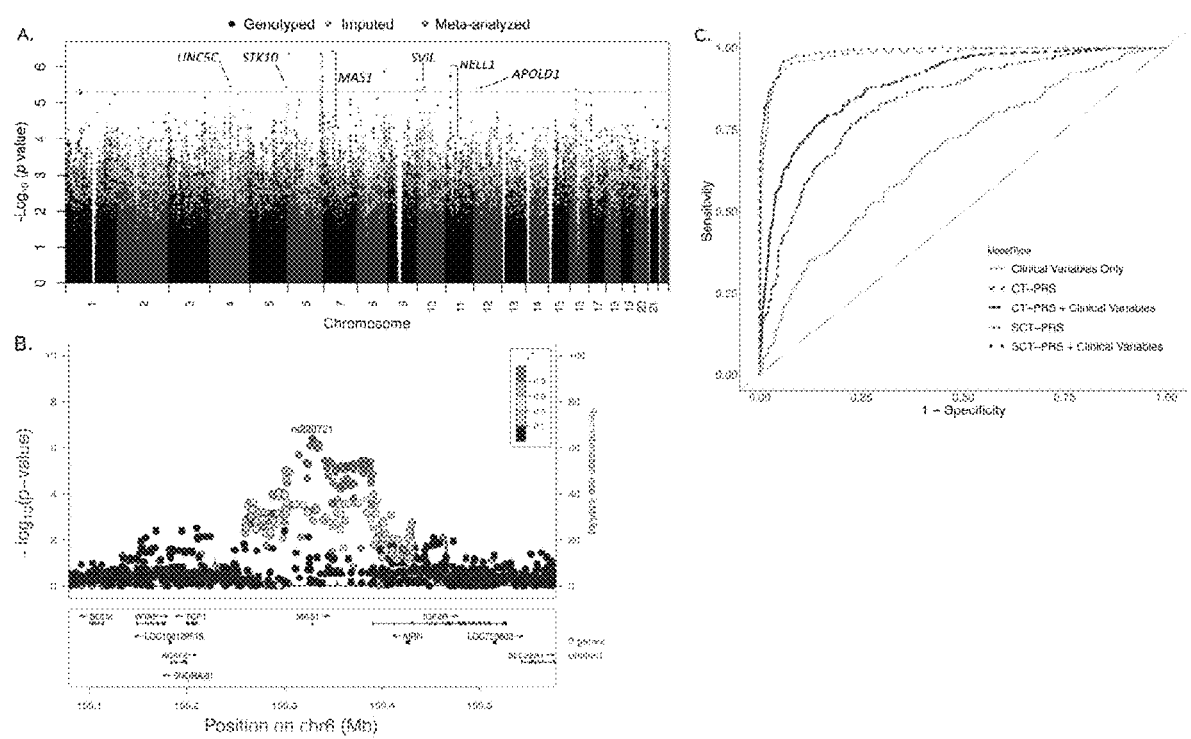
FIG. 5(A) is a Manhattan plot for the single nucleotide polymorphism associations with membership in C4 compared to all other groups.
FIG. 5(B) is a Locuszoom plot of SNPs located in MAML2.
FIG. 5(C) is a Locuszoom plot of SNPs located in NPY1R and NPY5R.

FIG. 5 represents a Genome Wide Association Analysis of Clinical Subgroup 4 (C4). FIG. 5(A) is a Manhattan plot for the single nucleotide polymorphism associations with membership in C4 compared to all other groups. Dashed lines represent thresholds for suggestive significance ($p<5\times10^{-6}$). FIG. 5(B) is a Locuszoom plot of SNPs located in MAS1. FIG. 5(C) is a Receiver operating characteristic (ROC) curve for a logistic regression model containing baseline clinical features only, clumping-thresholding polygenic score (CT-PS) only, CT-PS and baseline clinical features, stacking-clumping-thresholding polygenic score (SCT-PS) only, and SCT-PS and baseline clinical features. The SCT-PS model combined baseline clinical features outperformed the other models with an area under the curve (AUC) of 0.99. However, the SCT-PS only performed nearly as well (AUC=0.98) and was selected as the best model based on parsimony.

Figures 6A, 6B, 6C, 6D, 6E:
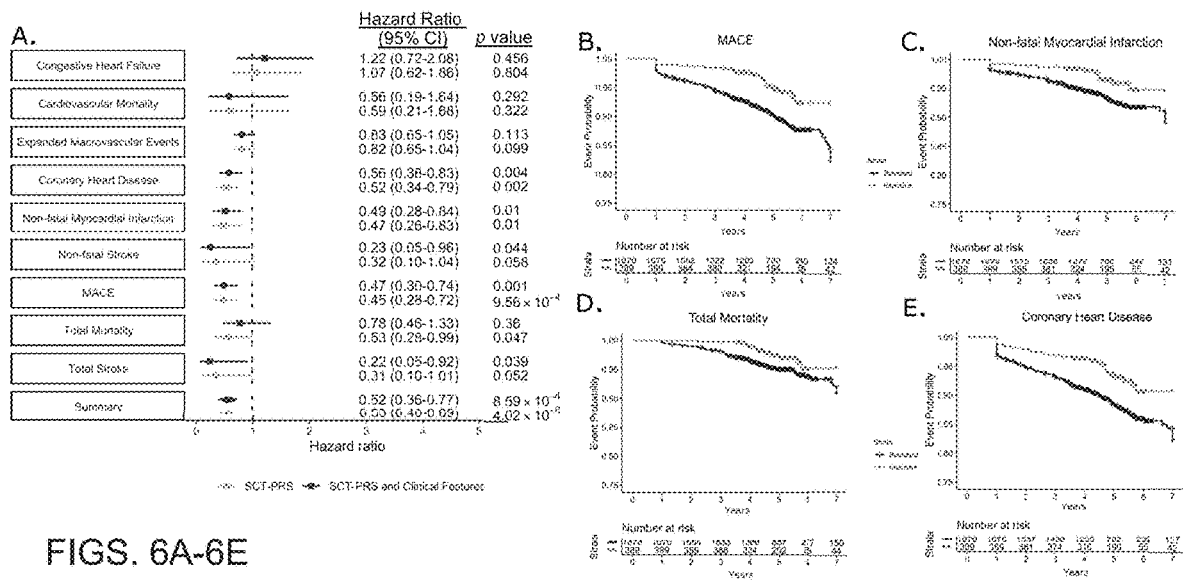
FIG. 6(A) a forest plot of hazard ratios (HR) between of individuals predicted to be in the C4 clinical group that received intensive glycemia treatment (from withheld test set) compared to those predicted to be in C4 that received standard treatment.
FIG. 6(B) is Kaplan-Meier curve comparing the incidence of MACE in those predicted to be in C4 that received intensive glycemia treatment compared to those predicted to be C4 that received standard treatment.
FIG. 6(C) is Kaplan-Meier curve comparing the incidence of non-fatal myocardial infarction in those predicted to be in C4 that received intensive glycemia treatment compared to those predicted to be C4 that received standard treatment.
FIG. 6(D) is Kaplan-Meier curve comparing total mortality in those predicted to be in C4 that received intensive glycemia treatment compared to those predicted to be C4 that received standard treatment.
FIG. 6(E) is Kaplan-Meier curve comparing the incidence of coronary heart disease in those predicted to be in C4 that received intensive glycemia treatment compared to those predicted to be C4 that received standard treatment.

FIG. 6(A) is a forest plot of hazard ratios (HR) between of individuals predicted to be in the C4 clinical group that received intensive glycemia treatment (from withheld test set) compared to those predicted to be in C4 that received standard treatment. Results from the SCT-PS with and without baseline clinical factors are shown. FIGS. 6(B), 6(C), 6(D), and 6(E) are Kaplan-Meier curves comparing the incidence in those predicted to be in C4 that received intensive glycemia treatment compared to those predicted to be C4 that received standard treatment for MACE [FIG. 6(B)], non-fatal myocardial infarction [FIG. 6(C)], total mortality[FIG. 6(D)], and coronary heart disease [FIG. 6(E)].

Figure 7:
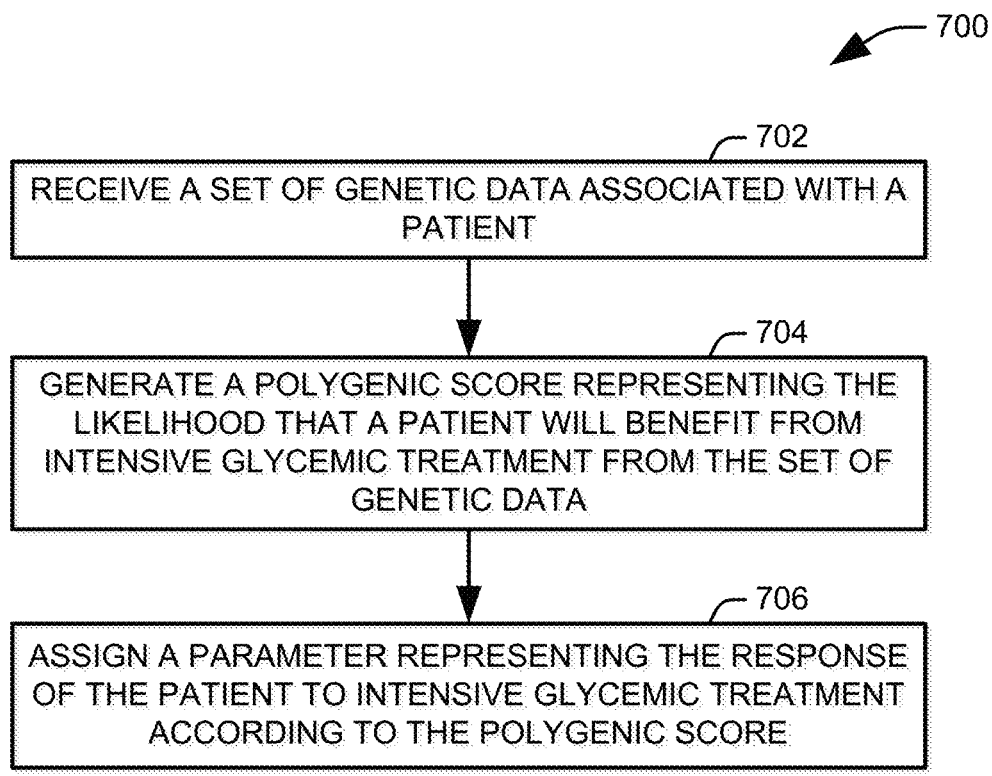
FIG. 7 illustrates one example of method for assigning a treatment to a patient.
Figure 8:
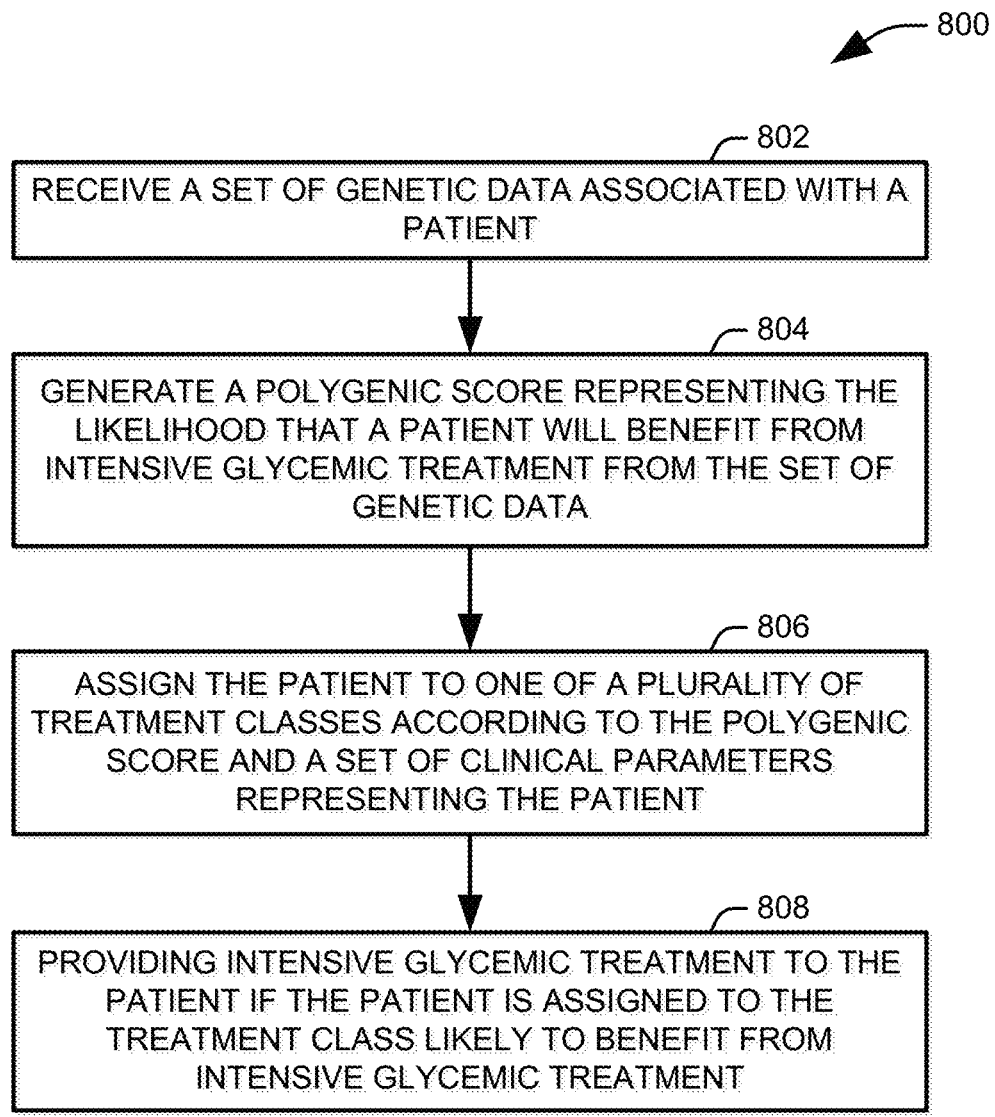
FIG. 8 illustrates an example of a method for assigning a treatment to a patient.

In view of the foregoing structural and functional features described above, example methods will be better appreciated with reference to FIGS. 7 and 8. While, for purposes of simplicity of explanation, the example methods of FIGS. 7 and 8 are shown and described as executing serially, it is to be understood and appreciated that the present examples are not limited by the illustrated order, as some actions could in other examples occur in different orders, multiple times and/or concurrently from that shown and described herein. Moreover, it is not necessary that all described actions be performed to implement a method.

FIG. 7 illustrates one example of method 700 for assigning a treatment to a patient. At 702, a set of genetic data representing a patient is received. In one implementation, the set of genetic data includes a series of parameters representing a set of single nucleotide polymorphisms (SNPs). At 704, a polygenic score is generated, representing the likelihood that a patient will benefit from intensive glycemia treatment, from the set of genetic data. In one implementation, each SNP in the set of genetic data is represented by an associated weight, and the polygenic score is computed as the sum of the weights of the SNPs associated with the patient.

At 706, a parameter representing a response of the patient to intensive glycemia treatment is assigned according to the polygenic score. For example, the polygenic score can be provided to a predictive model to assign the parameter. In one implementation, the predictive model can also utilize a set of clinical parameters representing the patient in assigning the parameter representing the expected response. Once the parameter has been assigned, the patient can be provided with intensive glycemia treatment if the parameter indicates that the patient will respond well to the treatment, or with an alternative treatment, such as treating the patient with GLP-1 receptor agonists or SGLT-2 inhibitors, if the parameter indicates that the patient will not respond well to intensive glycemia treatment.

FIG. 8 illustrates an example of a method 800 for assigning a treatment to a patient. At 802, a set of genetic data representing a patient is received. In one implementation, the set of genetic data includes a series of parameters representing a set of single nucleotide polymorphisms (SNPs), which can include SNPs in Mas1 proto-oncogene (MAS1), Neural EGFL Like 1 (NELL1), and Supervillin (SVIL), such as rs220721, rs1793004, and rs1270874. At 7804, a polygenic score representing the likelihood that a patient belongs to a treatment class likely to benefit from intensive glycemia treatment given the set of genetic data is generated. In one example, the set of generic data includes parameters representing the presence or absence of each of a plurality of single nucleotide polymorphisms in the patient. Each of the plurality of single nucleotide polymorphisms in the set of genetic data having an associated weight, and the polygenic score is generated by computing the sum of the weights associated with the single nucleotide polymorphisms present in the patient.

At 806, the patient is assigned to one of a plurality of treatment classes according to the polygenic score and a set of clinical parameters representing the patient. Each of the treatment classes can represent, for example, clusters of trajectories of HbA1c values for patients in response to intensive glycemia treatment determined via an unsupervised clustering process. Appropriate clinical parameters can include parameters representing a blood pressure of the patient, a measured of blood concentration of thyroid stimulating hormone for the patient, and alcohol consumption by the patient. At 7808, intensive glycemia treatment is provided to the patient if the patient is assigned to a treatment class likely to benefit from intensive glycemia treatment. For example, the patient can be treated with metformin, sulfonylureas, thiazolidinediones, and/or insulin products. Alternatively, the patient can be provided with an alternative treatment, such as GLP-1 receptor agonists or SGLT-2 inhibitors, if the patient is not assigned to a treatment class likely to benefit from intensive glycemia treatment.

Figure 9:
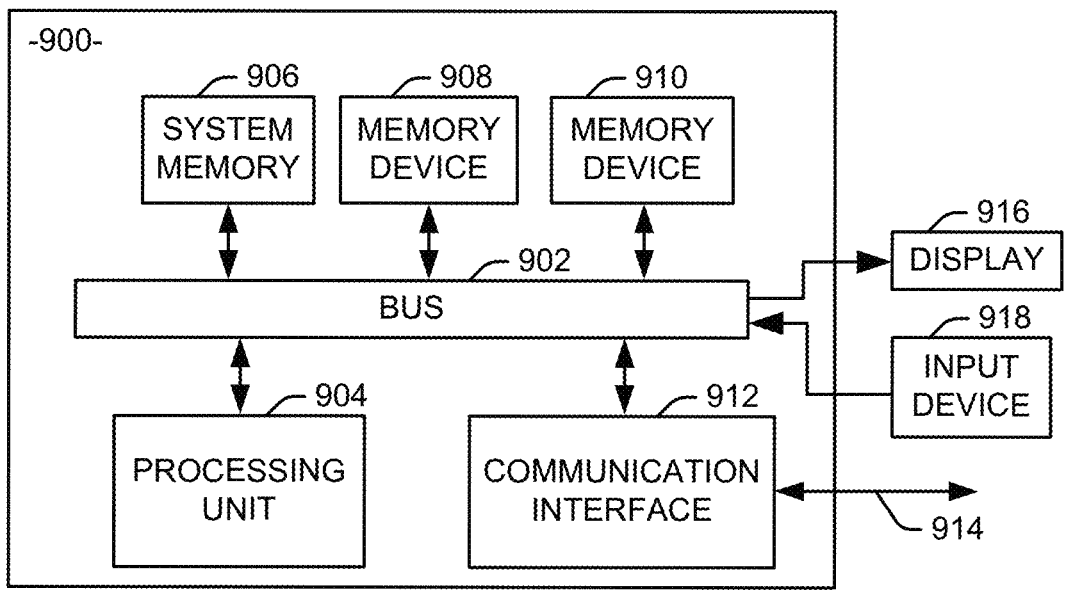
FIG. 9 is a schematic block diagram illustrating an exemplary system of hardware components.

FIG. 9 is a schematic block diagram illustrating an exemplary system 900 of hardware components capable of implementing examples of the systems and methods disclosed herein. The system 900 can include various systems and subsystems. The system 900 can be a personal computer, a laptop computer, a workstation, a computer system, an appliance, an application-specific integrated circuit (ASIC), a server, a server BladeCenter, a server farm, etc.

The system 900 can include a system bus 902, a processing unit 904, a system memory 906, memory devices 908 and 910, a communication interface 912 (e.g., a network interface), a communication link 914, a display 916 (e.g., a video screen), and an input device 918 (e.g., a keyboard, touch screen, and/or a mouse). The system bus 902 can be in communication with the processing unit 904 and the system memory 906. The additional memory devices 908 and 910, such as a hard disk drive, server, standalone database, or other non-volatile memory, can also be in communication with the system bus 902. The system bus 902 interconnects the processing unit 904, the memory devices 906-910, the communication interface 912, the display 916, and the input device 918. In some examples, the system bus 902 also interconnects an additional port (not shown), such as a universal serial bus (USB) port.

The processing unit 904 can be a computing device and can include an application-specific integrated circuit (ASIC). The processing unit 904 executes a set of instructions to implement the operations of examples disclosed herein. The processing unit can include a processing core.

The additional memory devices 906, 908, and 910 can store data, programs, instructions, database queries in text or compiled form, and any other information that may be needed to operate a computer. The memories 906, 908 and 910 can be implemented as computer-readable media (integrated or removable), such as a memory card, disk drive, compact disk (CD), or server accessible over a network. In certain examples, the memories 906, 908 and 910 can comprise text, images, video, and/or audio, portions of which can be available in formats comprehensible to human beings.

Additionally or alternatively, the system 900 can access an external data source or query source through the communication interface 912, which can communicate with the system bus 902 and the communication link 914.

In operation, the system 900 can be used to implement one or more parts of a system for selecting a course of treatment for a patient in accordance with the present invention. Computer executable logic for implementing the diagnostic system resides on one or more of the system memory 906, and the memory devices 908 and 910 in accordance with certain examples. The processing unit 904 executes one or more computer executable instructions originating from the system memory 906 and the memory devices 908 and 910. The term "computer readable medium" as used herein refers to a medium that participates in providing instructions to the processing unit 904 for execution. This medium may be distributed across multiple discrete assemblies all operatively connected to a common processor or set of related processors. Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A method for assigning a treatment to a patient, the method comprising:
   receiving a set of genetic data representing a patient at a system comprising a processor and a computer readable medium storing machine-readable instructions executable by the processor via a network interface;
   generating a polygenic score representing the likelihood that a patient will benefit from intensive glycemia treatment from the set of genetic data at a feature extractor implemented via the machine-readable instructions; and
   assigning a parameter representing a response of the patient to intensive glycemia treatment according to the polygenic score at a predictive model implemented via the machine-readable instructions;
   wherein the parameter representing the response of the patient to intensive glycemia treatment is a categorical parameter representing one of a plurality of treatment classes, each representing clusters of trajectories of HbA1c values for patients in response to intensive glycemia treatment determined via an unsupervised clustering process.

2. The method of claim 1, wherein assigning the parameter representing the response of the patient to intensive glycemia treatment comprises assigning the parameter representing the response of the patient to intensive glycemia treatment according to the polygenic score and a set of clinical parameters representing the patient.

3. The method of claim 2, wherein the set of clinical parameters includes a clinical parameter representing a blood pressure of the patient.

4. The method of claim 1, wherein the set of genetic data includes a parameter representing a single nucleotide polymorphism in one of Mas1 proto-oncogene (MAS1), Neural EGFL Like 1 (NELL1), and Supervillin (SVIL), the polygenic score being generated from at least the parameter representing the single nucleotide polymorphism.

5. The method of claim 1, wherein assigning the parameter representing the response of the patient to intensive glycemia treatment according to the polygenic score and a set of clinical parameters representing the patient comprises providing each of the polygenic score and the set of clinical parameters to a regression model.

6. The method of claim 1, further comprising treating the patient with one of metformin, sulfonylureas, thiazolidinediones, and insulin products if the parameter representing the response of the patient to intensive glycemia treatment indicates that the patient will respond well to intensive glycemia treatment.

7. The method of claim 1, further comprising treating the patient with one of GLP-1 receptor agonists and SGLT-2 inhibitors if the parameter representing the response of the patient to intensive glycemia treatment indicates that the patient will not respond well to intensive glycemia treatment.

8. The method of claim 1, wherein the set of genetic data includes a parameter representing one of a set of single nucleotide polymorphisms including rs220721, rs1793004, and rs1270874, the polygenic score being generated from at least the parameter representing the one of the set of single nucleotide polymorphisms.

9. The method of claim 1, wherein the set of generic data includes parameters representing the presence or absence of each of a plurality of single nucleotide polymorphisms in the patient and each of the plurality of single nucleotide polymorphisms in the set of genetic data having an associated weight, and generating the polygenic score comprises computing the sum of the weights associated with the single nucleotide polymorphisms present in the patient.

10. A system comprising:
a processor; and
a computer readable medium storing executable instructions for assigning a treatment to a patient, the executable instructions comprising:
a network interface that receives a set of genetic data representing a patient, the set of genetic data including a parameter representing one of a set of single nucleotide polymorphisms including rs220721, rs1793004, and rs1270874;
a feature extractor that generates a polygenic score representing the likelihood that a patient belongs to a treatment class likely to benefit from intensive glycemia treatment given the set of genetic data, the feature extractor generating the polygenic score from at least the parameter representing the single nucleotide polymorphism; and
a predictive model that assigns a parameter to the patient representing the response of the patient to intensive glycemia treatment as a weighted sum of the polygenic score and a set of clinical parameters representing the patient.

11. The system of claim 10, wherein the set of clinical parameters includes a clinical parameter representing a measurement of blood concentration of thyroid stimulating hormone for the patient.

12. The system of claim 10, wherein the set of genetic data includes a parameter representing a single nucleotide polymorphism in one of Mas1 proto-oncogene (MAS1), Neural EGFL Like 1 (NELL1), and Supervillin (SVIL), the feature extractor generating the polygenic score.

13. A method for assigning a treatment to a patient, the method comprising:
receiving a set of genetic data representing a patient at a system comprising a processor and a computer readable medium storing machine-readable instructions executable by the processor via a network interface;
generating a polygenic score representing the likelihood that a patient belongs to a treatment class likely to benefit from intensive glycemia treatment given the set of genetic data at a feature extractor implemented via the machine-readable instructions;
assigning the patient to one of a plurality of treatment classes according to the polygenic score and a set of clinical parameters representing the patient at a predictive model implemented via the machine-readable instructions, the plurality of treatment classes including the treatment class likely to benefit from intensive glycemia treatment;
providing intensive glycemia treatment to the patient if the patient is assigned to the treatment class likely to benefit from intensive glycemia treatment; and
treating the patient with one of GLP-1 receptor agonists and SGLT-2 inhibitors if the patient is not assigned to the treatment class likely to benefit from intensive glycemia treatment.

14. The method of claim 13, wherein each of the plurality of treatment classes represent clusters of trajectories of HbA1c values for patients in response to intensive glycemia treatment determined via an unsupervised clustering process.

15. The method of claim 13, wherein the set of clinical parameters includes at least a clinical parameter representing alcohol consumption by the patient.

16. The method of claim 13, wherein the set of genetic data includes a parameter representing a single nucleotide polymorphism in one of Mas1 proto-oncogene (MAS1), Neural EGFL Like 1 (NELL1), and Supervillin (SVIL), the polygenic score being generated from at least the parameter representing the single nucleotide polymorphism.

17. The method of claim 13, further comprising treating the patient with one of GLP-1 receptor agonists and SGLT-2 inhibitors if the patient is not assigned to the treatment class likely to benefit from intensive glycemia treatment.

18. A system comprising:
a processor; and
a computer readable medium storing executable instructions for assigning a treatment to a patient, the executable instructions comprising:
a network interface that receives a set of genetic data representing a patient, the set of generic data including parameters representing the presence or absence of each of a plurality of single nucleotide polymorphisms in the patient;

a feature extractor that generates a polygenic score representing the likelihood that a patient belongs to a treatment class likely to benefit from intensive glycemia treatment given the set of genetic data, the feature extractor computing the sum of weights associated with the single nucleotide polymorphisms present in the patient to provide the polygenic score; and a predictive model, trained on training data representing patients for whom an associated treatment class is known, that assigns a parameter to the patient representing the response of the patient to intensive glycemia treatment according to the polygenic score and a set of clinical parameters representing the patient.

19. A system comprising:

a processor; and a computer readable medium storing executable instructions for assigning a treatment to a patient, the executable instructions comprising:

a network interface that receives a set of genetic data representing a patient, the set of genetic data including a parameter representing a single nucleotide polymorphism in one of Mas1 proto-oncogene (MAS1), Neural EGFL Like 1 (NELL1), and Supervillin (SVIL);

a feature extractor that generates a polygenic score representing the likelihood that a patient belongs to a treatment class likely to benefit from intensive glycemia treatment given the set of genetic data, the feature extractor generating the polygenic score from at least the parameter representing the single nucleotide polymorphism; and a predictive model, trained on training data representing patients for whom an associated treatment class is known, that assigns a parameter to the patient representing the response of the patient to intensive glycemia treatment according to the polygenic score and a set of clinical parameters representing the patient.

* * * * *